United States Patent [19]
Long et al.

[11] Patent Number: 5,505,096
[45] Date of Patent: Apr. 9, 1996

[54] PARTICULATE MATERIAL SAMPLING APPARATUS

[75] Inventors: Armistead M. Long, Knoxville; John B. Long, Louisville, both of Tenn.

[73] Assignee: Heron Holdings, Knoxville, Tenn.

[21] Appl. No.: 314,139

[22] Filed: Sep. 28, 1994

[51] Int. Cl.$^6$ ............................................. G01N 1/00
[52] U.S. Cl. ...................... 73/863.53; 73/863.56
[58] Field of Search ......................... 73/863/863.41, 73/863.42, 863.45, 863.51–863.53, 863.56

[56] References Cited

U.S. PATENT DOCUMENTS

| | | | |
|---|---|---|---|
| 3,472,079 | 10/1969 | Cordell | 73/863.51 |
| 4,619,149 | 10/1986 | Long . | |
| 4,796,476 | 1/1989 | Long . | |
| 4,884,462 | 12/1989 | Long . | |
| 4,919,000 | 4/1990 | Long | 73/863.91 |
| 4,951,511 | 8/1990 | Perron et al. | 73/863.56 |
| 4,955,242 | 9/1990 | Long . | |

FOREIGN PATENT DOCUMENTS 1353605  5/1974  United Kingdom ................ 73/863.56

OTHER PUBLICATIONS

Sales Bulletin: TEMA Inc., Cincinnati, Ohio, Feb. 17, 1986 Laboratory Divider.
Reference Text: American Society For Testing Materials; 1988 Annual Book of ASTM Standards; Section 5–Petroleum Products, Lubricants and Fossil Fuels; vol. 05.05 Gaseous Fuels Coal and Coke, pp. 222, 224, 225.
Reference Text: International Organization for Standardization ISO 3082, First Edition 1987–06–01, p. 27.
Product Catalog: Gilson Company, Inc., Catalog 93–1 (Published Jan. 1993) pp. 50–59.
Product Catalog: F. Kurt Retsch GMBH & Co. KG; Laboratory Sample Divider Printed Jun. 1987.
Technical Paper: E. Reiners and P. Mohrhauer, Equipment for the Preparation of Bulk Samples, Bulk Solids Handling, vol. 13, No. 2, May 1993, p. 321.

*Primary Examiner*—Robert Raevis
*Attorney, Agent, or Firm*—Luedeka, Neely & Graham

[57] ABSTRACT

A spin riffle sampling apparatus distributes a sample source quantity of particulate material in a predetermined number of increments, 60 for example, to each of a smaller number, 4 for example, of radially disposed bins on a rotating platform. The bins include top openings which pass through a falling zone of material to receive material into the bins. The width dimension of each opening decreases with increasing radial displacement from the axis of rotation of the platform. The bins also may be forwardly pitched relative to the direction of rotation of the platform so as to induce a down draft to control dusting.

25 Claims, 4 Drawing Sheets

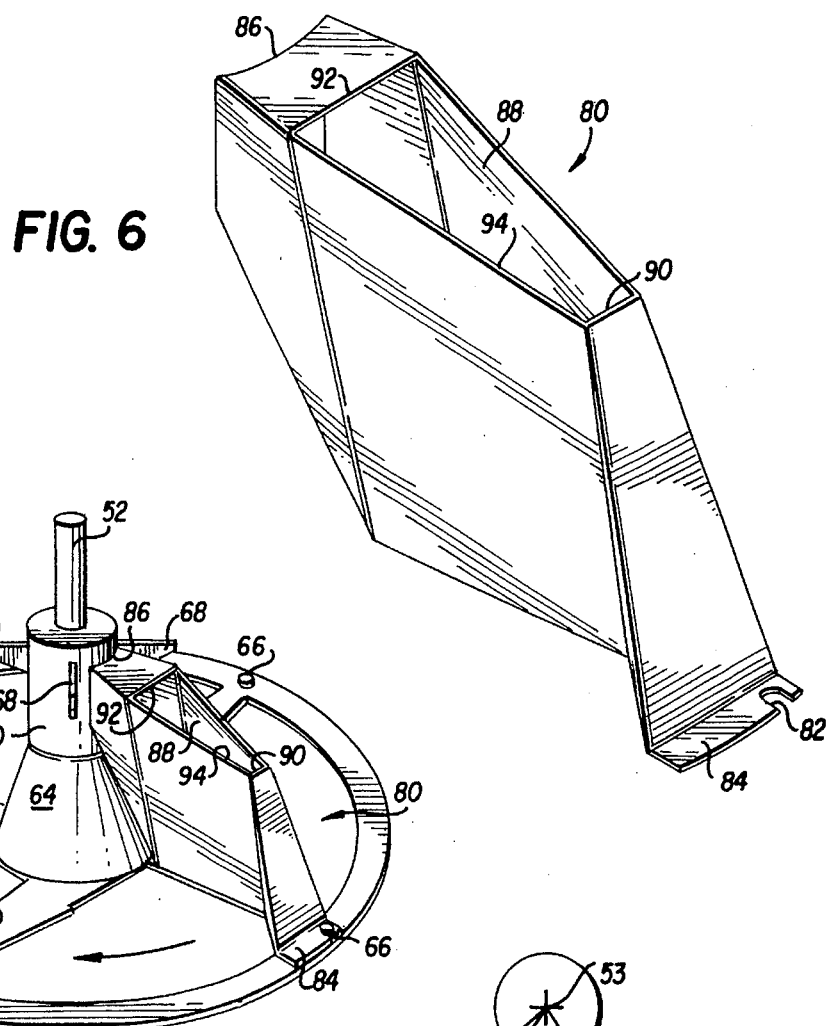
FIG. 6
FIG. 7
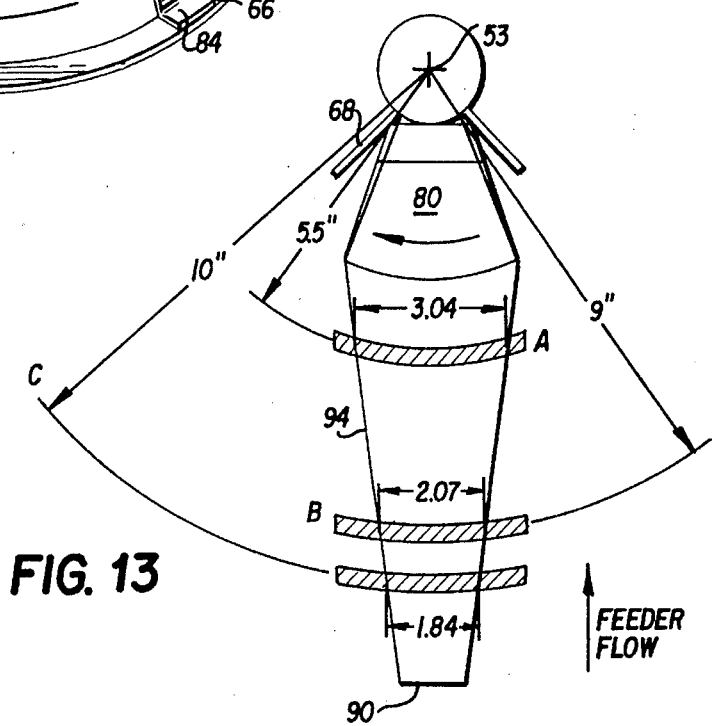
FIG. 13

PARTICULATE MATERIAL SAMPLING APPARATUS

BACKGROUND OF THE INVENTION

1. Field of Invention

The present invention relates to means and methods for isolating a representative sample of a large quantity of particulate material such as coal.

Particulate material of relatively high value such as coal is frequently tested for properties or characteristics such as energy value (BTU per pound), metal content and/or moisture. Such tests are carried out on small samples of the subject material extracted from the primary shipment, source or supply. In the interest of accuracy and consistency, test samples are extracted and prepared with great care and methodical discipline to eliminate as many sources of weight, volume or moisture bias as economically feasible. The objective is a statistically "representative" sample wherein every particle in a sample source has equal opportunity to be in the selected volume.

For example, "representative" may be translated as a homogenous, 1000 g quantity of a 1000 ton shipment or flow increment. As produced in nature, the energy value of a coal seam is stratiated with some segments of greater heating value than others. However, with all the strata produced and combined, the seam product heating value and other properties may be relatively constant. Nevertheless it is necessary to test the product at shipment to determine its properties in relation to predetermined criteria, such as purchase contract specifications. The testing procedure must, of necessity, involve only small increments of the total quality of material. A proper test procedure must produce results which are confidently representative of the entire mass.

Pursuant to a commonly practiced methodology, a randomly selected cross sectional increment of coal or ore production as deposited on a conveyor is extracted completely from the conveyor. Depending on previous processing, the sample increment may be further pulverized and size screened. Commonly, this crushed and screened sample is divided into four identical test batches, one for the producer, one for the user and two held in abeyance for re-testing if necessary.

Many variables affect the momentary production rate that coal is deposited on a production conveyor, but the variance is manifest from the weight of coal on the conveyor per unit length of conveyor. Consequently, the batch magnitude of sample source extracted from the conveyor may fluctuate 200% or more. For example, the total sample source weight may vary from 25 pounds to 75 pounds of material.

Against this extracted sample source batch variation, the four, for example, formal samples to be isolated for actual testing are usually specified to be a small, uniform quantity such as 1 Kg., for example. Moreover, each formal sample may be specified as being composed of a designated number, 60, for example, of uniformly spaced, cross-sectional slices of the sample source batch. Meeting this specification of 60 increments for each of the four, 1000g formal samples, requires the sample source batch to be divided into 240 slices but only 16.6 g of each slice to be actually used for formal sample composition.

The prior art has developed both rotary and linear sample dividers by which a given sample source batch is distributed into a predetermined number of increments. None of these prior instruments, however, are capable of a randomly selected proportionalization of the sample source batch to achieve the necessary percentage of a specified number of increments in the specified number of samples to correctly allocate a variable weight source batch to a predetermined number of fixed weight formal samples.

SUMMARY

The present invention provides an integrated, wheel mounted, portable sample dividing apparatus which includes a live-bottom, sample delivery conveyor for delivering a metered flow rate of particulate material comprising a sloping side wall supply hopper positioned over a small belt conveyor. The belt traveling velocity is controlled by an adjustable speed reduction drive unit. At the removal end of the hopper, where the moving belt carries material from the underside of the hopper, an adjustable height screed gate controls the height of a sample material delivery bed deposited on the belt for delivery to a proportionalizing chute at the discharge end of the belt. The angular setting of the proportionalizing chute determines the freefall landing zone radius for belt carried sample material relative to a rotational speed controlled turntable which carries split sample receiver bins.

Each receiving bin is radially disposed about the rotating axis of the turntable and fabricated with an open top area, the width of which decreases with increasing radial displacement from the rotational axis.

Additionally, each split receiving bin is disposed on an angular pitch relative to the turntable rotational axis, such pitch being functional as a propeller for dust suppression by inducing a down draft movement of air past the bin as it rotates.

The conveyor belt velocity and screed gate are adjusted to deliver the sample quantity of material over the period of time necessary for the designated number of cuts as dictated by the rotational speed of the turntable. For example, if the turntable is set to rotate at 30 rpm and 60 sample cuts for each of four splits are designated, the belt speed and screed gate are set to deliver a constant bed depth of sample material for two minutes.

$$\left( 2 \text{ min.} \times 30 \, \tfrac{\text{rev}}{\text{min}} = 60 \text{ rev, i.e. } 60 \text{ cuts} \right)$$

Simultaneously, the conveyor proportionalizing chute is angularly positioned at a bin mouth width (i.e. turntable radius) which corresponds to receiving 1/60 of a total sample split per revolution. Thus, if the total sample split for each bin is to be 1000 g, 16.6 g of material will be deposited in each bin per revolution of the turntable.

Excess material delivered by the conveyor belt and not captured within a bin is bypassed to a receiver cabinet as discard.

Near the bottom of the receiver cabinet there may be an air draft induction port to draw air past the proportionalizing chute and receiver bins as a supplemental dust suppression mechanism.

An operational objective of this invention, therefore, is to provide a particulate material sample preparation apparatus having at least two material flow control devices for coordinated apportionment of a variable quantity of material sample source to a predetermined quantity of such material in each of a fixed number of sample receiving bins and in a predetermined number of distribution cuts.

Another object of the present invention is to provide spin riffle sample collection bins having reverse radius mouth openings so that the ratio of bin mouth opening width varies with the turntable radius dimension.

A further object of the present invention is to provide a particulate material sample supply belt with a variable position discharge cute to control the material and quantity delivered to a rotating collection bin mouth opening.

An additional object of the invention is to provide spin riffle sample receiving bins with an upstanding pitch leaning into the rotational direction to impel an axial air displacement by rotation about the turntable axis.

DESCRIPTION OF THE DRAWINGS

Relative to the several figures of the drawings:

FIG. 6 is a pictorial view of the present invention sample collection bin.

FIG. 7 is a pictorial view of the sample distribution system turntable and combined collection bin.

FIG. 13 is a schematic of the sample collection bin opening and material distribution pattern.

DESCRIPTION OF THE PREFERRED EMBODIMENT

Figure 1:
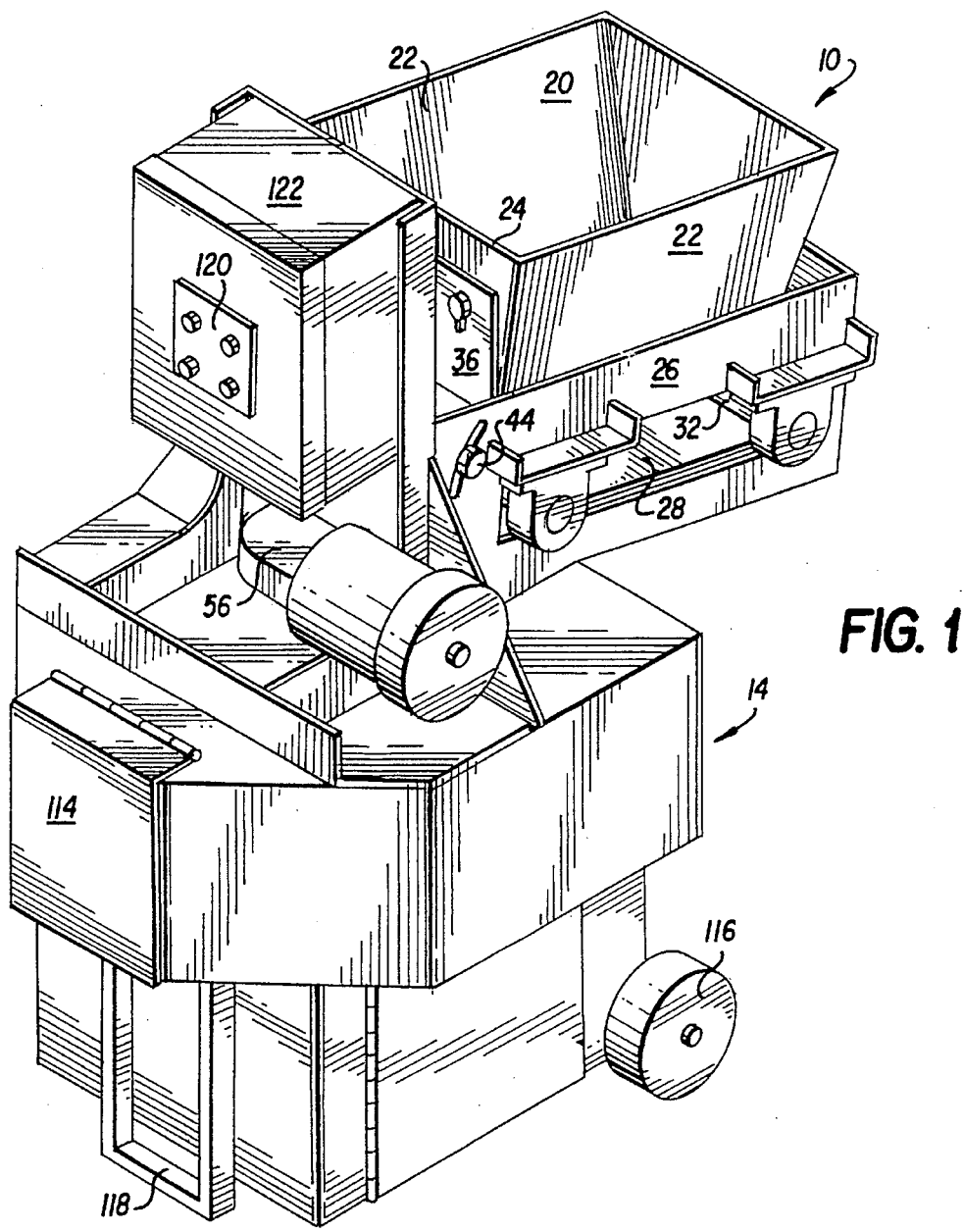
FIG. 1 is a pictorial view of the present invention.
Figure 2:
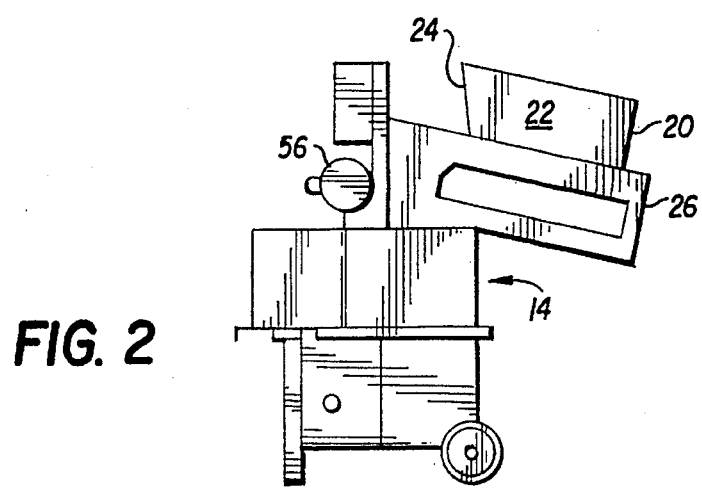
FIG. 2 is an orthographic side elevation of the present invention.
Figure 3:
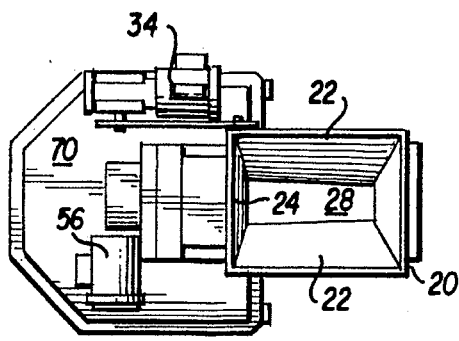
FIG. 3 is an orthographic plan view of the present invention.
Figure 4:
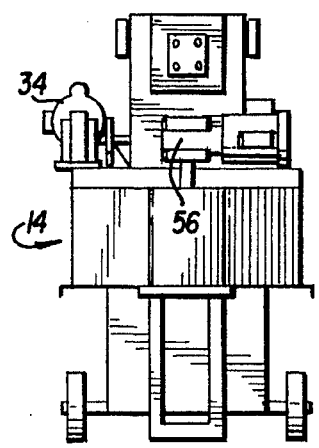
FIG. 4 is an orthographic end view of the present invention.
Figure 5:
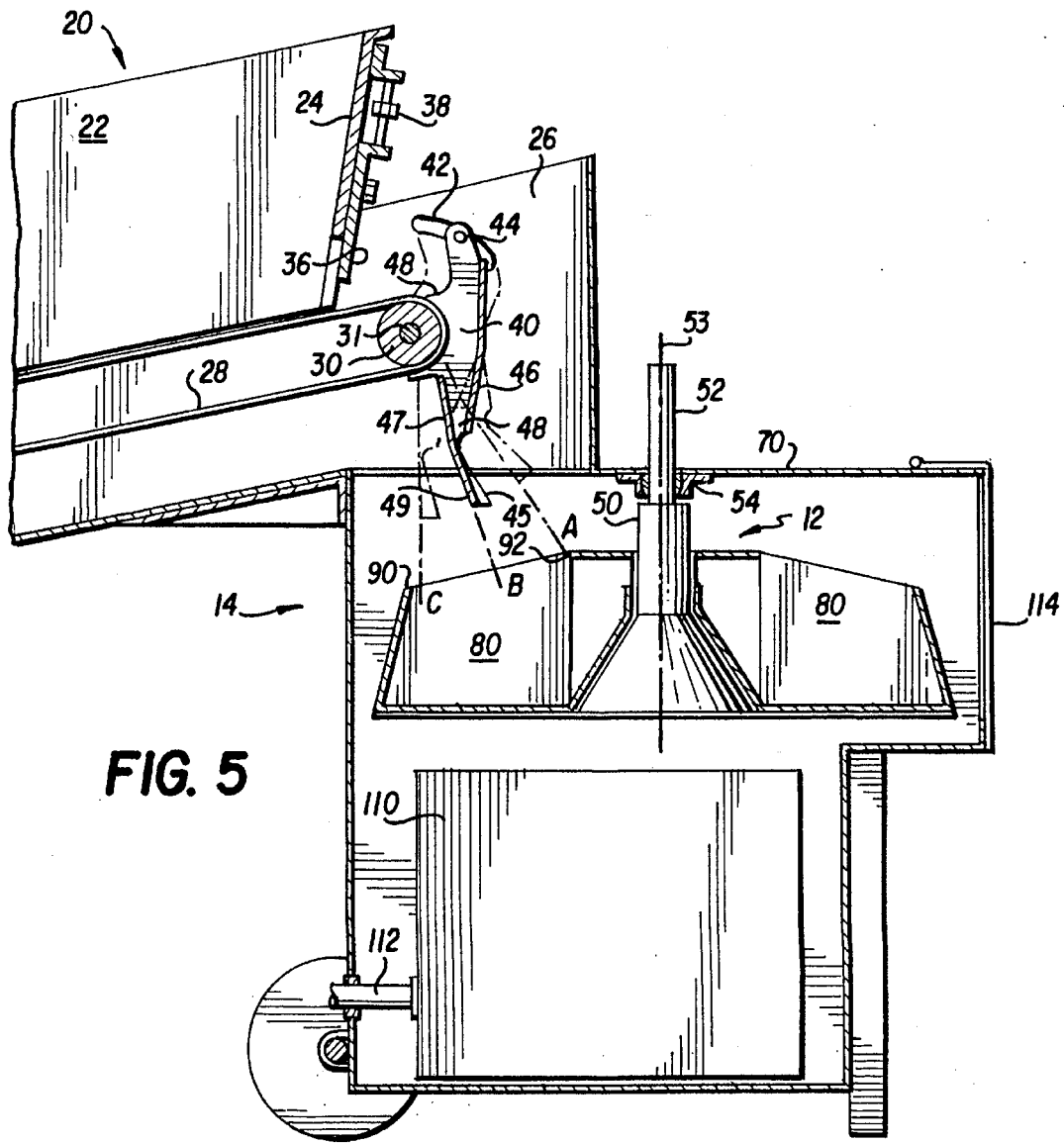
FIG. 5 is a sectioned elevational view of the present invention.
Figure 8:
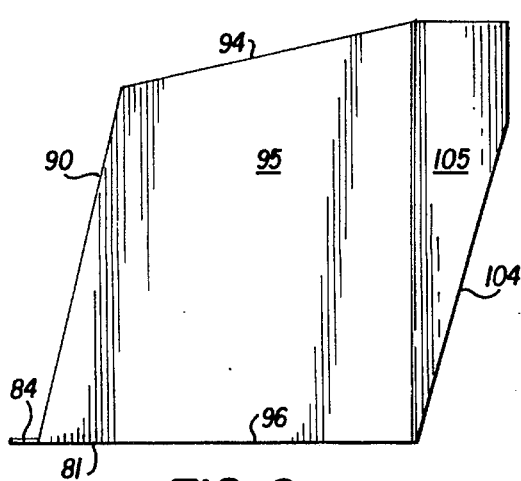
FIG. 8 is a side elevation of the present invention sample collection bin.
Figure 9:
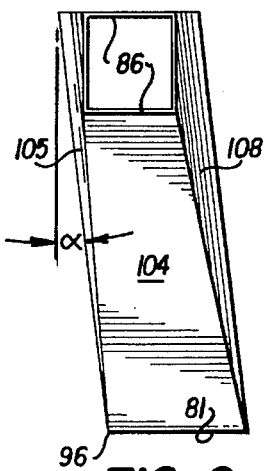
FIG. 9 is a radially inner end elevation of the sample collection bin.
Figure 10:
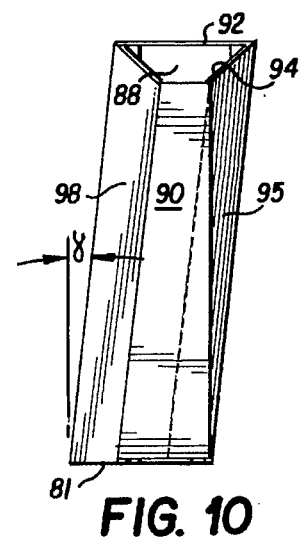
FIG. 10 is a radially outer end elevation of the sample collection bin.
Figure 11:
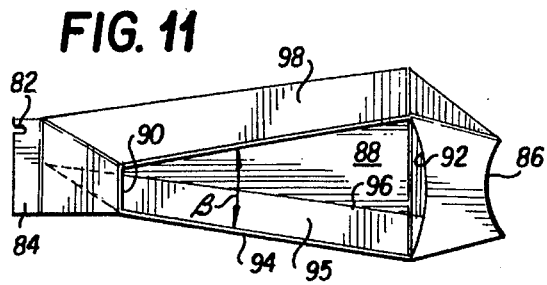
FIG. 11 is a top plan view of the sample collection bin.
Figure 12:
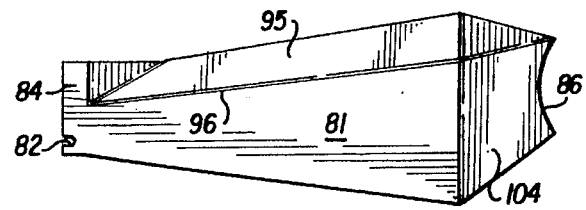
FIG. 12 is a bottom plan view of the sample collection bin.

The preferred embodiment of the present invention illustrated by FIG. 1 includes, as major assembly components, a material delivery unit 10, a sample distribution unit 12, and surrounding dust control cabinetry 14. The sample distribution unit 12 is substantially enclosed by the cabinetry 14 as shown by FIG. 5.

The material delivery unit 10 comprises a hopper 20 having sloping side walls 22 flanking a delivery end 24 secured to box frame 26. A conveyor belt is coursed around a pair of carrier rolls 30 and 32 mounted for rotation between bearing pedestals. The forward carrier roll 32 is powered by the motor and variable reduction drive unit 34.

Delivery end wall 24 supports a gate screed 36 adjustably positioned by jackscrews 38. At the delivery end 30 of the belt 28, material carried by the belt is cut to a uniform thickness against the lower edge of the screed 36. Additionally, the upper or discharge end of the conveyor belt 28 supports a discharge guide chute 40 that is adjustably positioned about the rotational axis of belt carrier roll 30. Arced slots 42 in the sidewalls of box frame 26 accommodate a position securing clamp 44 to hold the chute 40 at a desired position within an available range of arcuate freedom as represented by the phantom lines of FIG. 5.

Discharge chute 40 is constructed with a backsplash shield 46 that converges with the guide trough 47 to form an elongated, narrow slice opening 48 which spreads the flow of particulate material into a shallow depth delivery stream between cheek plates 45 at the lateral boundaries of a discharge lip 49. The significance and need for a shallow depth delivery stream will be subsequently developed with respect to an expanded explanation of the invention operation.

The sample distribution unit 12 is best illustrated by FIG. 5 with the power and control components omitted for clarity. Basically, the distribution unit comprises a suspended turntable 50 having a drive shaft 52 secured within a bearing unit 54 for rotational freedom and axial support. The bearing unit 54 is anchored to a top wall 70 of the dust control cabinet 14. With respect to FIGS. 1-4, the turntable 50 is driven by a motor and variable reduction drive unit 56 about vertical axis 53.

The lower end of the drive shaft 52 supports an open platform wheel 58 having a circular rim 60 connected by radially offset spokes 62 to the drive shaft 52. Conical shrouding 64 sheds excess particulate material from the flat, central hub region where the spokes 62 junction with the drive shaft. Open space between the spokes 62 permits such excess particulate material to fall past the wheel 58 into the cabinet reject bin 110. Dowel pins or lugs 66 anchored to the turntable rim 60 serve to anchor each of the sample collection bins 80 in place along a respective supporting spoke 62. An open side socket 82 in a bottom tab 84 extension from a bin bottom panel 81 receives a respective dowel pin 66 to prevent lateral and radially outward displacement of the outside end of the bin base.

The radially interior ends of the bins 80 are confined by radial abutments 68 secured to and projecting from the shaft 52. Additionally, a concave profile saddle 86 to the bin interior mating with the shaft 52 cylindrical surface restrains the bin from turntable displacement.

Particular note should be taken of two construction characteristics of the present sample collection bin 80. First, the collection bins are constructed with an angular "lean" to the height. This "lean" is oriented to "lean into" the direction of turntable rotation and is proportioned to displace air parallel with the turntable axis of rotation from the top to the bottom for dust suppression. Appropriately, the "lean" represents propeller pitch whereby the top of the bin is angularly advanced about the turntable rotational axis relative to the bin bottom with a substantially smooth air displacement surface connecting the top and bottom as bin sides.

With respect to FIGS. 8–12 showing a full orthographic development of the bin 80, it is seen that the leading top edge 94 of the bin mouth is connected by the leading wall 95 to the leading bottom edge 96. Definitively, the descriptive term "leading" refers to the direction of rotation in which the bin 80 is carried. The pitch described above is the angle e the side walls 95 and 98 are given relative to the vertical plane of the turntable 50 rotational axis 53. A representative value of angle $\alpha$ may be in the range of 10° to 30° with about 15° preferred in most cases.

The leaning side walls 95 and 98 are faired into the saddle 86 edges by an end panel 104 and respective side panels 105 and 108 for smooth axial air displacement parallel with the platform wheel rotational axis 53.

It will also be noted from the drawings that the top plane of each bin corresponding to the open bin mouth is cut an angle to the horizontal. This top plane angle is the consequence of a substantially equidistant displacement of the radially inner (92) and outer (90) mouth ledges from the axis 31 of discharge guide chute 40.

Collaterally, the bin pitch also suppresses dust generated by the riffling process by cutting cleanly into the material free falling flow stream with the leading upper mouth edge 94. Lateral striking of the bin leading sidewalls by the free falling material stream to free dust size particles is minimized.

A second construction characteristic of the collection bin relates to the radially converging bin mouth 88 whereby the outer ends 90 of the mouth 88 are of less width than the radially inner ends 92. A preferred mouth side convergent angle β is about 15° but considerable latitude of variation from the preferred is available. This will be understood relative to one of the invention operational principles explained with reference to FIG. 13 which illustrates a bin 80 secured to a rotating turntable 58. One bin 80 is shown for purposes of simplicity and explanation. Operationally, a preferred embodiment will carry four such bins 80. However, the principles explained and described herein may be applied to any number of sample collection bins, more or less than four.

The following development will assume that four samples will be taken of 1000 g each in respective bins 80. Each of the four samples will be composed of 60 cuts or increments from the sample source which will be extracted from the hopper 20. This sample source is to be distributed in 3 min (180 sec.), is of 50 lb/ft$^3$ density and will be delivered from the discharge lip 49 of the chute 40 in an arced free-fall section that is 6"×0.25" (1.5 in$^2$).

Due to production rate variables, sample extraction devices have produced three weight quantities of sample source material: A—25 lbs.; B—60 lbs.; and, C— 75 lbs. These different quantities of source material are to be reduced to 4, 1000 g batches, each having 60 slices of the sample source. Two variables will be determined for each of the three sample source batch quantities: (1) the belt 28 material delivery speed and (2) the radial distance of the chute 40 discharge flow from the turntable axis 53.

CASE A 25 lb. of 50 lb/ft$^3$ #8 particulate material are to be distributed to four rotating bins 80 in 60 cuts each, 1 cut per bin per revolution. Accordingly, 11,363 g of material will be distributed in 60 revolutions, i.e., 190 g/rev. However, because only a 1000 g sample is desired in each bin i.e., 16.6 g/rev, only 8.8% of the total flow stream per bin is accepted, the remainder being discard.

As a given, the 25# sample source must be delivered in 180 seconds and received in 60 cuts i.e. revolutions. Bin 80 rotational speed therefore will be 0.33 rev/sec. Consequently, the 190 g of material to be delivered per revolution will flow at the rate of 63.3 g/sec.

50 lb/ft$^3$ density material translates to 13.2 g/in$^3$. If confined to a 6"×0.25" (1.5 in$^2$) sectional area flow ribbon from the chute 40 discharge lip 49, that material will be distributed at rate of 19.7 g/in of belt length. At this belt distribution density, the 63.3 g/sec required material delivery rate for condition A will require a belt speed of 3.2 in./sec.

The angularity of chute 40 is set to center the free-fall material arc at a bin mouth width which corresponds to 8.8% of the rotational circumference about rotational axis 58. Specifically, an 11 in. dia circle (5.5 in. radius) has a 34.54 in. circumference. 8.8% of that circumference is 3.04 in. which corresponds to the width of the bin mouth 88 at 5.5 in. from the rotational axis 53.

CASE B 60 lb of 50 lb/ft$^3$, #8 particulate material will be distributed in 60 revolutions, i.e. 455 g/rev. 16.6 g/rev of that 455 g/rev represents 3.6% of the total. An 18 in. diameter (9 in. radius) has a circumference of 56.52 in. 3.6% of the circumference corresponds to a 2.07 in. bin mouth width.

455 g/rev. delivered to a bin 80 rotating at 0.33 rev/sec. requires a flow rate of 151.6 g/sec. If distributed along the material free-fall zone at 19.7 g/in., the belt 28 must travel 7.7 in./sec.

CASE C 75 lb of 50 lb/ft$^3$, #8 particulate material will be distributed in 60 revolutions, i.e. 568 g/rev. 16.6 g/rev. of that 568 g/rev represents 2.9% of the total. A 20 in. dia (10 in radius) circle has a circumference of 62.8 in. 2.9% of the circumference corresponds to a 1.84 in. bin mouth width.

568 g/rev delivered to a bin 80 rotating at 0.33 rev./sec. requires a flow rate of 189.3 g/sec. If distributed along the material free-fall zone at 19.7 g/in., the belt 28 must travel at 9.6 in/sec.

It has been explained that only 1000 g, for example, of sample source material was accepted for each of 4 sampling bins and the remainder of the sample source discarded. This discarded material is collected in a reject bin 110 enclosed by the dust control cabinetry 14. In addition to the downdraft induced by the pitched bins 80 on the turntable 50, the reject bin 110 may be internally swept by a partial vacuum source 112 such as a portable shop vacuum.

A hatch door 114 facilitates removal of the sample collection bins 80 when the process has been completed. Wheels 116 ease the transportability of the invention whereas jackstand 118 helps to stabilize and level the invention during operation.

Figure 14A:
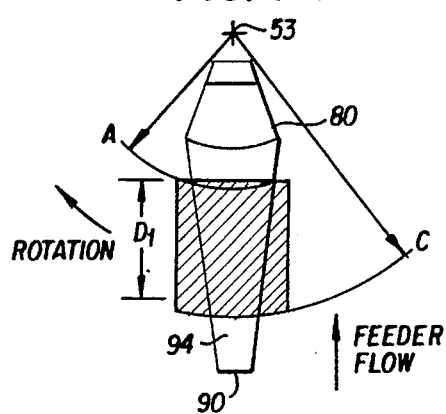
FIGS. 14A and 14B schematically compare a thick free-fall zone depth to the preferred shallow depth.
Figure 14B:
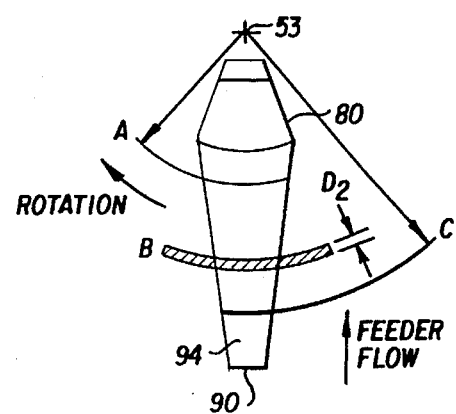

With an understanding of how the material source delivery conveyor rate is coordinated with the radial positionment of the material free-fall zone from the platform rotational axis 53, it will be recognized that for a given material flow rate into the guide chute 40, the percentage of all free-fall flow from the guide chute 40 that actually enters a collection bin 80 is greater for fall lines (A) that are closer to the platform rotational axis 53 than those fall lines (C) that are more remote from the rotational axis 53. Consequently if there is a significant material free-fall depth, as represented by $D_1$ of FIG. 14A, a greater percentage of top flow material from the delivery conveyor would be deposited in the bin than bottom flow material. Such bias arises by the influence of gravity and vibration which drives a separation of particles in a moving stream by weight, density or volume. Hence, for example, there would be a disproportionate number of dense particles at the bottom of conveyor supported material flow than at the top. If the flow depth is significant, as represented by $D_1$ of FIG. 14A, a greater percentage of those dense particles would be excluded from the accepted sample because the corresponding free-fall accept zone is more restrictive than that corresponding to the top of the conveyor material flow. A very small free-fall stream depth, as represented relatively by dimension $D_2$ of FIG. 14B, greatly mitigates such bias potential in the flow stream.

Manual start/stop controls 120 for the two motor units 34 and 56 are mounted on the cover of a motor control enclosure 122. The presently preferred embodiment provides manual mechanical speed change for the belt 28 and turntable 50 drive units 34 and 56, respectively. It will be understood that remote speed control and monitoring may be provided to regulate the belt 28 and turntable 50 speeds electrically and provide instrumentation to report the speed status.

Along the same principle, automatic data processing units may be connected and programmed to maintain a coordinated relationship between a specific sample source quantity and a final formal sample.

Having fully described my invention, obvious mechanical and electrical equivalencies will occur to those of ordinary skill. For example, the supply belt 28 may be replaced by a screw or auger conveyor. Obviously, other physical configurations may be devised to funnel the material extracted from the supply hopper 20 to the radial position relative to the turntable 50 and the bin mouth 88. As our invention, however,

We claim:

1. An apparatus for preparing a representative sample of particulate material comprising:

a conveyor for delivering a stream of particulate material at a metered flow rate into a free falling zone;

a rotatable support for carrying a material receiving container about a rotational axis and along a circular path through said free falling zone; and, a material receiving container having a top opening delineated by length and width whereby the top opening width diminishes along the length from one length end to an opposite length end, said container being positioned upon said rotatable support with said length aligned substantially radially from said rotational axis and with said one end most proximate of said axis.

2. An apparatus as described by claim 1 wherein said conveyor comprises a speed variable belt positioned below a material supply hopper.

3. An apparatus as described by claim 2 wherein said hopper comprises an adjustably positioned screeding gate disposed above said belt for regulating the depth of material on said belt extracted from said hopper.

4. An apparatus as described by claim 1 wherein said conveyor comprises a discharge controller for selecting a particular location for depositing said material stream within said free falling zone.

5. An apparatus as described by claim 4 wherein said discharge controller is adjusted to channel said material stream to a predetermined radial location relative to said support rotational axis.

6. An apparatus as described by claim 4 wherein said free falling zone comprises a radially projected area relative to said support rotational axis, said radially projecting area traversing an annular area swept by said receiving container opening.

7. An apparatus as described by claim 1 wherein said receiving container opening comprises a polygon having a radially outer end width and a radially inner end width between respectively connecting side walls, said inner end width being greater than said outer end width.

8. An apparatus as described by claim 1 wherein said free falling zone, said rotating support and said material receiving container are enclosed within a partially evacuated dust control cabinet.

9. An apparatus as described by claim 1 wherein said material receiving container is detachably independent of said support.

10. An apparatus as described by claim 9 wherein said support carries a plurality of said receiving containers.

11. An apparatus as described by claim 1 wherein said receiving container top opening is angularly advanced about said rotational axis relative to a bottom portion of said receiving container with an air displacement wall surface therebetween whereby air is displaced along said rotational axis by rotation of said receiving container about said axis.

12. An apparatus for preparing a representative sample of particulate material comprising:

a conveyor for delivering a stream of particulate material at a metered flow rate into a selected position within a free falling zone;

a rotating support for carrying an open top material receiving container about a rotational axis and along a circular path through said free falling zone so that a portion of material delivered into said free falling zone enters said container through said open top; and a material receiving container having a top opening connected by sidewall surfaces to a bottom surface, said top opening being defined by length and width dimensions with said width diminishing progressively along said length from one to an opposite length end, said container adapted to be positioned on said rotating support with said opening length aligned substantially radially from said rotational axis and with a greater width more proximate of said axis, said top opening also being positioned relative to said bottom surface at an angularly advanced location about said rotational axis whereby air is displaced along said sidewalls from said top toward said bottom by rotation of said receiving container about said axis.

13. An apparatus as described by claim 12 wherein said conveyor comprises a speed variable belt positioned below a material supply hopper.

14. An apparatus as described by claim 13 wherein said hopper comprises an adjustably positioned screeding gate disposed above said belt for regulating the depth of material on said belt extracted from said hopper.

15. An apparatus as described by claim 12 wherein said conveyor comprises a discharge controller for selecting a particular location for depositing said material stream within said free falling zone.

16. An apparatus as described by claim 15 wherein said discharge controller is adjusted to channel said material stream to a predetermined radial location relative to said support rotational axis.

17. An apparatus as described by claim 15 wherein said free falling zone comprises a radially projected area relative to said support rotational axis, said radially projected area traversing an annular area swept by said geometric container open top.

18. An apparatus as described by claim 12 wherein said free falling zone, said rotating support and said material receiving container are enclosed within a partially evacuated dust control cabinet.

19. An apparatus as described by claim 12 wherein said material receiving container is detachably independent of said support.

20. An apparatus as described by claim 19 wherein said support carries a plurality of said receiving containers.

21. A method of preparing a representative sample of particulate material comprising the steps of:

delivering a stream of particulate material at a selected flow rate to a selectively positionable discharge channel;

providing support for rotation of a material receiving container about a rotational axis;

providing a material receiving container having an open top geometry with width and length whereby the open top width is substantially convergent from one length end to an opposite length end disposing said receiving container on said container support for rotation therewith and with said open top length aligned substantially radially from said rotational axis with said one length end more proximate of said rotational axis, and, directing a discharge stream of said material from said discharge channel into said material receiving container through said open top.

22. An method as described by claim 21 wherein said container open tog traverses an annular rotational zone.

23. A method as described by claim 21 wherein an air displacement along said rotational axis is induced past said receiving container top toward a bottom of said container.

24. A method as described by claim 23 wherein said air displacement is at least partially induced by fabrication of said receiving container with structural pitch from said top to said bottom.

25. A method as described by claim 23 wherein said receiving container open top rotatively leads the bottom thereof to at least partially propel displaced air over said container from top to bottom.

* * * * *

UNITED STATES PATENT AND TRADEMARK OFFICE
CERTIFICATE OF CORRECTION

PATENT NO. : 5,505,096
DATED : April 9, 1996
INVENTOR(S) : Armistead M. Long & John B. Long It is certified that error appears in the above-indentified patent and that said Letters Patent is hereby corrected as shown below:

```
Column 4, line 56, delete "e" and insert -- a --.

Column 5, line 61, between "at and rate", insert -- a --.

Claim 22, line 14, delete "tog" and insert -- top --.
```

Signed and Sealed this

Twentieth Day of August, 1996

Attest:

BRUCE LEHMAN

*Attesting Officer*  *Commissioner of Patents and Trademarks*